(12) United States Patent
Martin

(10) Patent No.: US 10,918,450 B2
(45) Date of Patent: *Feb. 16, 2021

(54) CONTROLLING A LASER SURGICAL DEVICE WITH A SENSATION GENERATOR AND A GESTURE DETECTOR

(71) Applicant: Novartis AG, Basel (CH)

(72) Inventor: Peter Martin, Velden (DE)

(73) Assignee: Alcon Inc.

( * ) Notice: Subject to any disclaimer, the term of this patent is extended or adjusted under 35 U.S.C. 154(b) by 105 days.

This patent is subject to a terminal disclaimer.

(21) Appl. No.: 16/034,202

(22) Filed: Jul. 12, 2018

(65) Prior Publication Data

US 2019/0029769 A1 Jan. 31, 2019

Related U.S. Application Data

(60) Provisional application No. 62/537,837, filed on Jul. 27, 2017.

(51) Int. Cl.
*A61B 34/00* (2016.01)
*G06F 3/01* (2006.01)
(Continued)

(52) U.S. Cl.
CPC .............. *A61B 34/74* (2016.02); *A61B 18/20* (2013.01); *A61B 34/25* (2016.02); *A61B 34/76* (2016.02); *A61F 9/008* (2013.01); *A61F 9/00804* (2013.01); *A61F 9/00827* (2013.01); *G06F 3/016* (2013.01); *G06F 3/017* (2013.01); *G06F 3/04817* (2013.01); *G06F 3/04847* (2013.01);
(Continued)

(58) Field of Classification Search
CPC ......... A61B 18/20; A61B 34/25; A61B 34/74; A61B 34/76; A61F 9/008; G06F 3/016; G06F 3/017; G06F 3/04847; G06F 3/04842

See application file for complete search history.

(56) References Cited

U.S. PATENT DOCUMENTS

2006/0207978 A1* 9/2006 Rizun ..................... A61B 34/76
219/121.83
2011/0295243 A1 12/2011 Peyman
(Continued)

FOREIGN PATENT DOCUMENTS

WO 2014183792 A1 11/2014
WO 2016132144 A1 8/2016

*Primary Examiner* — Eric D. Bertram

(57) ABSTRACT

In certain embodiments, a system for controlling a laser device comprises a laser device, a haptic sensation generator, a gesture detector, and a computer. The laser device generates a laser beam with a focal point to perform a procedure on a patient. The haptic sensation generator generates an acoustic field that projects a sensory pattern onto a user, where the sensory pattern operates as a user controller related to the procedure. The gesture detector detects a gesture of the user interacting with the user controller, and provides a description of the gesture. The computer: instructs the haptic sensation generator to generate the acoustic field that projects the sensory pattern operating as the user controller; receives the description of the gesture of the user interacting with the user controller; and provides instructions to perform an operation corresponding to the gesture.

16 Claims, 7 Drawing Sheets

(51) Int. Cl.
*G06F 3/0484* (2013.01)
*G06F 3/16* (2006.01)
*A61F 9/008* (2006.01)
*G06F 3/0481* (2013.01)
*A61B 18/20* (2006.01)
*A61B 90/00* (2016.01)
*A61B 17/00* (2006.01)
*A61B 90/30* (2016.01)
*A61B 18/00* (2006.01)

(52) U.S. Cl.
CPC .............. *G06F 3/167* (2013.01); *A61B 90/30* (2016.02); *A61B 2017/00115* (2013.01); *A61B 2017/00199* (2013.01); *A61B 2017/00207* (2013.01); *A61B 2017/00212* (2013.01); *A61B 2018/00946* (2013.01); *A61B 2090/371* (2016.02); *A61F 2009/00863* (2013.01); *A61F 2009/00872* (2013.01); *G06F 3/04842* (2013.01)

(56) References Cited

U.S. PATENT DOCUMENTS

| | | |
|---|---|---|
| 2014/0114296 A1 | 4/2014 | Woodley et al. |
| 2015/0192995 A1* | 7/2015 | Subramanian .......... G06F 3/016 340/407.1 |
| 2015/0277735 A1 | 10/2015 | Gibson |
| 2015/0290031 A1* | 10/2015 | Wellhoefer ............. A61F 9/008 345/156 |
| 2017/0004819 A1 | 1/2017 | Ochiai et al. |
| 2017/0123499 A1 | 5/2017 | Eid |

* cited by examiner

CONTROLLING A LASER SURGICAL DEVICE WITH A SENSATION GENERATOR AND A GESTURE DETECTOR

TECHNICAL FIELD

The present disclosure relates generally to controlling surgical laser devices, and more specifically to controlling a laser surgical device with a sensation generator and a gesture detector.

BACKGROUND

Surgeons use laser surgical devices to shape, cut, and remove tissues of the body. For example, laser surgical devices (e.g., LASIK devices) are used to reshape the cornea to perform refractive correction on an eye. The devices have controllers (e.g., knobs, switches, footswitches, buttons, or graphic elements) that the surgeon uses to control features of the device. For example, a knob can be used to increase or decrease the illumination of the surgical field. In certain situations, concerns about potential contamination of surgical devices have led to the development of touchless controllers, such as devices that are controlled by the surgeon's hand gestures.

BRIEF SUMMARY

A system for controlling a laser device comprises a laser device, a haptic sensation generator, a gesture detector, and a computer. The laser device generates a laser beam with a focal point to perform a procedure on a patient. The haptic sensation generator generates an acoustic field that projects a sensory pattern onto a user, where the sensory pattern operates as a user controller related to the procedure. The gesture detector detects a gesture of the user interacting with the user controller, and provides a description of the gesture. The computer: instructs the haptic sensation generator to generate the acoustic field that projects the sensory pattern operating as the user controller; receives the description of the gesture of the user interacting with the user controller; and provides instructions to perform an operation corresponding to the gesture.

In certain embodiments, the system comprises a display that displays a graphic element corresponding to the user controller. The computer instructs the display to display the graphic element and a graphic response to the gesture of the user interacting with the user controller. In certain embodiments, the computer can provide the instructions to the laser device to move the focal point or to change an illumination of the procedure. In certain embodiments, the system comprises a patient support that supports the patient relative to the laser device. The computer provides the instructions the patient support to move the patient relative to the laser device. A first example of the user controller is a command button, and the gesture of the user interacting with the user controller comprises selecting the command button. A second example of the user controller is a knob, and the gesture of the user interacting with the user controller comprises turning the knob. A third example of the user controller is a slider, and the gesture of the user interacting with the user controller comprises sliding the slider.

A method for controlling a laser device comprises: generating, with a laser device, a laser beam with a focal point to perform a procedure on a patient; generating, with a haptic sensation generator, an acoustic field that projects a sensory pattern onto a user, the sensory pattern operating as a user controller related to the procedure; detecting, with a gesture detector, a gesture of the user interacting with the user controller; providing, by the gesture detector, a description of the gesture; instructing, with a computer, the haptic sensation generator to generate the acoustic field that projects the sensory pattern operating as the user controller; receiving, at the computer, the description of the gesture of the user interacting with the user controller; and providing, by the computer, instructions to perform an operation corresponding to the gesture. Certain embodiments may include features described above with respect to the system for controlling a laser device.

BRIEF DESCRIPTION OF THE DRAWINGS

Embodiments of the present disclosure are described by way of example in greater detail with reference to the attached figures, in which.

DESCRIPTION OF EXAMPLE EMBODIMENTS

Referring now to the description and drawings, example embodiments of the disclosed apparatuses, systems, and methods are described in detail. As apparent to a person of ordinary skill in the field, the disclosed embodiments are exemplary and not exhaustive of all possible embodiments.

Figure 1:
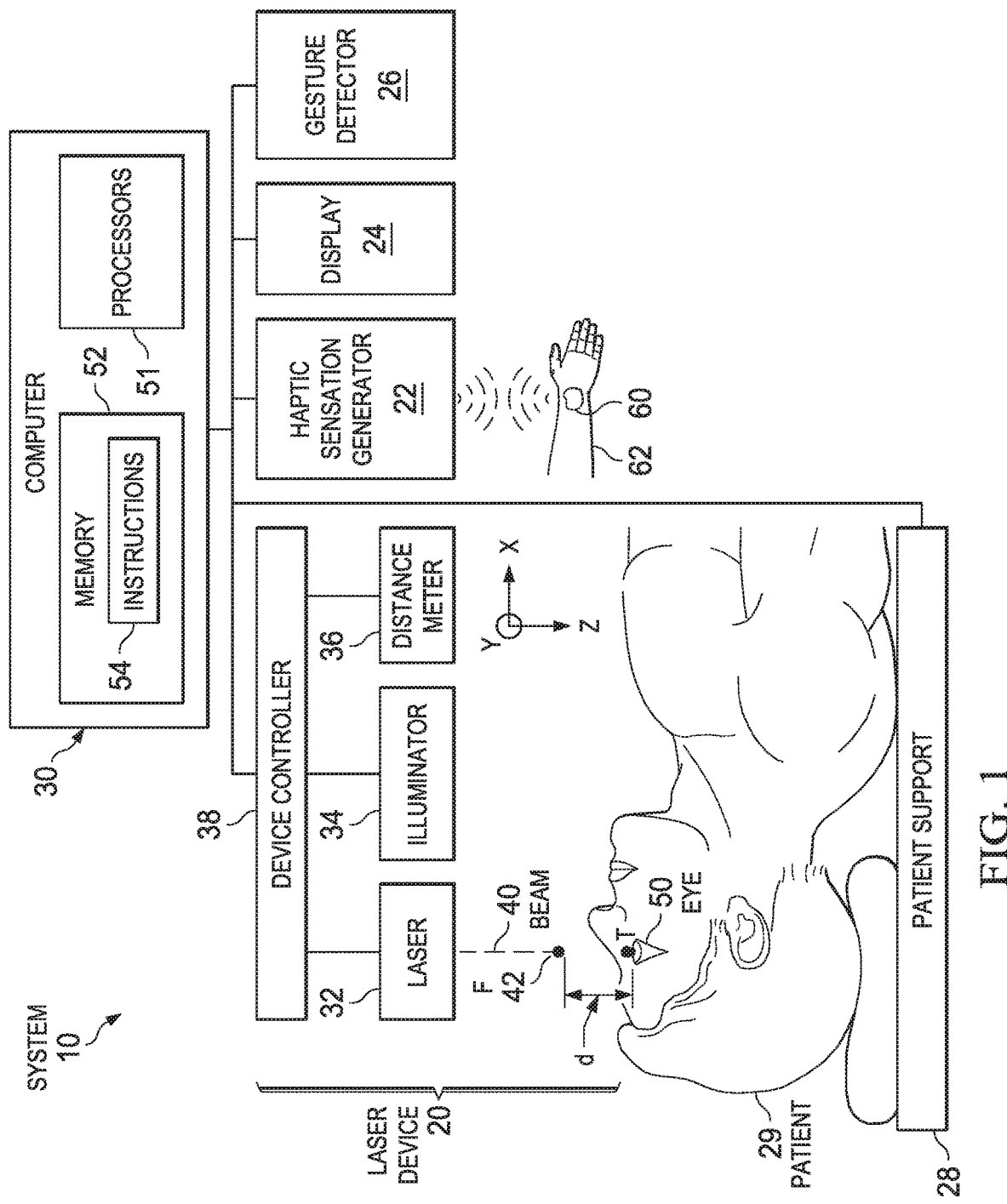
FIG. 1 illustrates an embodiment of a system for controlling a laser device using a haptic sensory pattern.

FIG. 1 illustrates an embodiment of a system 10 for controlling a laser device 20 using a haptic sensory pattern. System 10 allows for control of laser device 20 without requiring the user (e.g., surgeon) to touch laser device 20, which reduces contamination of laser device 20.

In certain embodiments, system 10 comprises laser device 20, a haptic sensation generator 22, a display 24, a gesture detector 26, a patient support 28, and a computer 30 coupled as shown. Laser device 20 generates a laser beam used to perform a medical procedure on a patient 29, e.g., ophthalmic surgery on an eye. Haptic sensation generator 22 generates an acoustic field that projects a sensory pattern onto a user that the user can feel. In some cases, the sensory pattern may provide information to the user. For example, to indicate the distance between the focal point of the laser beam and a target, the pattern may feel larger to indicate a longer distance or smaller to indicate a shorter distance. In other cases, the sensory pattern may operate as a user controller that the user can interact with to make an adjustment in system 10. For example, the pattern may feel like a knob the user can turn.

In certain embodiments, display 24 displays a graphic element. In some cases, the graphic element may provide a visual representation of the information provided to the user. For example, to indicate the distance between the focal point and target, the graphic element may be larger to indicate a longer distance or smaller to indicate a shorter distance. In other cases, the graphic element may provide a visual representation of the user controller. For example, the graphic element may look like a knob. Gesture detector 26 detects a gesture of the user, such as a gesture of the user interacting with the user controller. For example, the gesture may be the user turning something like a knob. Patient support 28 (e.g., a patient bed or a headrest) supports a patient 29 relative to the laser device. Computer 30 sends instructions to laser device 20, haptic sensation generator 22, display 24, gesture detector 26, and/or patient support 28 to control their operation.

Laser device 20 generates a laser beam 40. In certain embodiments, laser device 20 comprises a laser 32, an illuminator 34, a distance meter 36, and a device controller computer 28. Laser 32 generates a laser beam 40 with a focal point F. Laser beam 40 may define an xyz-coordinate system. The axis of laser beam 40 defines the z-axis, which is normal to the xy-plane. Examples of laser 32 include an excimer laser (an ultraviolet laser with a pulse repetition rate of ~100 Hz to 8 kHz and a pulse duration of ~10 ns to 30 ns) and a femtosecond laser (an ultrashort pulse laser that can emit light in the infrared or ultraviolet wavelength range). An excimer laser generates a laser beam that can photoablate tissue in order to, e.g., reshape corneal tissue. A femtosecond laser generates a laser beam that can create laser-induced optical breakdowns (LIOBs) in tissue in order to, e.g., create an incision in corneal tissue. Laser device 20 may include other components that control beam 40, e.g., a scanner, optical elements, and a focusing objective.

The procedure may be any suitable medical procedure on patient 29 that cuts or shapes tissue of patient 29, such as an ophthalmic surgical procedure on an eye 50 of patient 29. In these cases, focal point F may be directed to a target T of eye 50. Target T may be a point on the surface of eye 50 or a point within tissue, e.g., corneal, lens, or retinal tissue, of eye 50. In other embodiments, target T may be a point on the surface of the skin or a point within epidermal tissue.

Illuminator 34 comprises any suitable light source that generates light (e.g., visible or infrared light) that can illuminate the area of the procedure. The intensity and/or direction may be controlled by device controller computer 38.

Distance meter 36 measures distance, e.g., the distance between focal point F and target T of eye 50. Any suitable distance meter 36 may be used. For example, distance meter 36 may have diodes that direct non-parallel light beams toward eye 50 to form light spots on the surface of eye 50. As eye 50 is adjusted closer to or farther away from laser 32, the spots move closer together or farther apart. In some cases, the spots can overlap when eye 50 is at a specific distance from laser 32. Distance meter 36 may have a camera that views the spots to determine the distance from laser 32. Device controller computer 88 may be a computer that controls the operation of laser device 20 by sending instructions to its components, e.g., laser 32, illuminator 34, and distance meter 36.

Haptic sensation generator 22 generates an acoustic field that projects a sensory pattern 60 onto a user 62. Sensory pattern 60 is a tactile sensation that can be felt by user 62, e.g., a human. In the case of a human, sensory pattern 60 is usually felt by a hand, but can be felt by any part of the human body. In certain cases, sensory pattern 60 operates as a user controller, so user 62 can interact with sensory pattern 60 by making a gesture that sends a command. Any suitable haptic sensation generator 22 may be used, e.g., an ULTRAHAPTICS TOUCH device. Any suitable sensory pattern 60 may be projected, and examples of patterns 60 are described with reference to FIGS. 2A-3B.

In certain embodiments, haptic sensation generator 22 includes an array of transducers that projects an acoustic field onto a human. Each transducer outputs an acoustic wave that yields the resulting acoustic field. The frequency of the field is controlled such that the human perceives a haptic sensation. In certain embodiments, the acoustic waves comprise ultrasound waves that are modulated at a frequency between 0.1 Hz to 500 Hz.

Display 24 displays a graphic element. Display 24 may be a computer monitor that presents visual information, such as a graphic element. A graphic element is an image, typically with a size, color, and/or shape that has a specific meaning. For example, a graphic element may represent a user controller, and the element may be displayed when a sensory pattern 60 that operates as the user controller is generated for user 62. In the example, user 62 can gesture to interact with sensory pattern 60 to send a command to system 10. Another graphic element may be a graphic response to the gesture that is detected by gesture detector 26. For example, the graphic element may be highlighting to indicate user 62 has gestured to interact with sensory pattern 60. Examples of graphic elements are described with reference to FIGS. 2A-3B.

Gesture detector 26 detects a gesture of the user. A gesture is a movement of the user, e.g., movement of a hand, foot, head, or other part of the user. The movement may be in any suitable direction at any suitable speed. Examples of gestures are described with reference to FIGS. 2A-2E. Gesture detector 26 may use any suitable detector to detect gestures, such as a depth-aware camera (e.g., structured light or time-of-flight camera), a stereo camera, or a gesture-based controller. After detecting a gesture, gesture detector 26 may provide a description of the gesture to computer 30.

Computer 30 controls the operation of system 10, and includes processors 51 and a memory 52. Processors 51 carry out operations according to instructions 54, which are stored in memory 52. Computer 30 can perform any suitable operations. For example, computer 30 receives a measurement of the distance between focal point F and target T from distance meter 36; determines the pattern corresponding to the distance according to a function in which the distance is a variable; and instructs haptic sensation generator 22 to generate an acoustic field that projects the determined pattern. Any suitable function may be used; examples of functions are described with reference to FIGS. 3A-3B.

As another example, computer 30 instructs haptic sensation generator 22 to generate an acoustic field that projects a sensory pattern corresponding to a user controller, and instructs display 24 to display a graphic element representing the user controller. Computer 30 receives a description of a gesture of user 62 interacting with the user controller. Computer 30 then instructs display 24 to display a graphic response to the gesture. Examples of graphic responses are described with reference to FIGS. 2A-3B. Computer 30 also determines an operation corresponding to the gesture and provides instructions to perform the operation. The operation may be determined using a table that associates gestures with operations, and may be performed by a component of system 10. Examples of such operations include: instructing laser device 20 to move focal point F or beam 40 closer to or farther away from target T or eye 50; instructing illuminator 34 to change illumination, e.g., the brightness or direction of illumination; or instructing patient support 28 to move patient 29 relative to laser device 20, e.g., farther away from or closer to in the z-direction or along the xy-plane.

FIGS. 2A-2E illustrate examples of sensory pattern 60 operating as a user controller to control components of system 10. In the examples, haptic sensation generator 22 generates a sensory pattern 60 (60a-e) that operates as a user controller, and display 24 displays a graphic element 70 (70a-e) representing the user controller. User 62 gestures to interact with sensory pattern 60 to provide input to system 10 with the user controller. Gesture detector 26 detects the gesture, and display 24 displays a graphic response 72 (72a-e) to the gesture. Computer 30 (shown in FIG. 1) sends instructions to the components of system 10 to perform the operation.

Figure 2A:
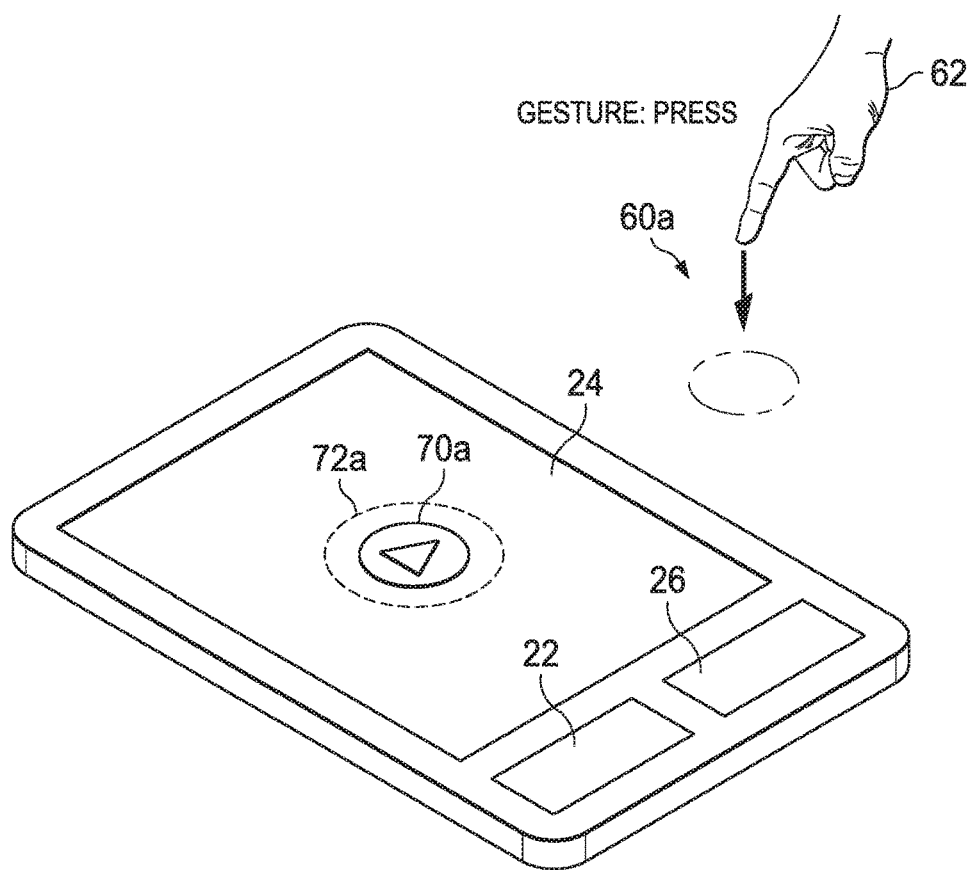
FIGS. 2A-2E illustrate examples of a sensory pattern operating as a user controller to control components of the system of FIG. 1.

In FIG. 2A, the user controller is a command button that user 62 can select to trigger an event represented by the button. Haptic sensation generator 22 generates a sensory pattern 60a that operates as the button. Display 24 displays a button element 70a representing the button. User 62 gestures to interact with sensory pattern 60a to select the button, e.g., user 62 moves her hand to press sensory pattern 60a to select the button. Display 24 displays a graphic response 72a representing the pressing, e.g., the button graphic 70a may be highlighted to show the button has been selected.

Figure 2B:
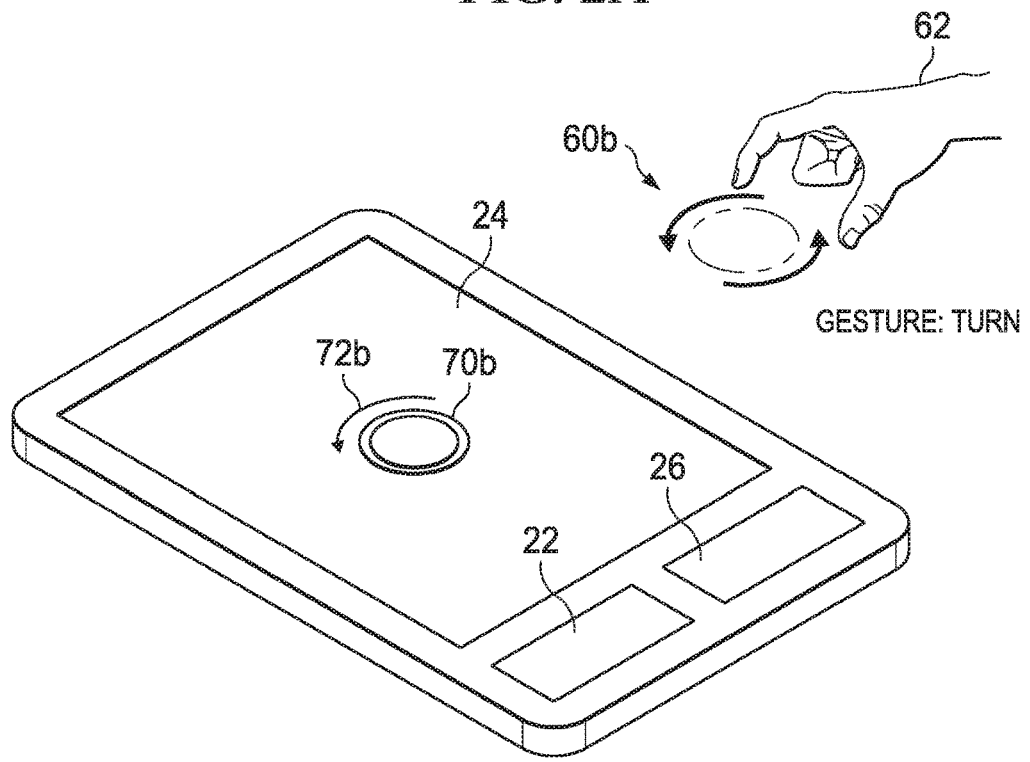

In FIG. 2B, the user controller is a knob that user 62 can turn to select a value indicated by the knob. Haptic sensation generator 22 generates a sensory pattern 60b that operates as the knob. Display 24 displays a knob element 70b representing the knob. User 62 gestures to interact with sensory pattern 60b to turn the knob, e.g., user 62 moves her hand to turn sensory pattern 60b to select a value indicated by the knob. Display 24 displays a graphic response 72b representing the selection, e.g., the selected value may be highlighted.

Figure 2C:
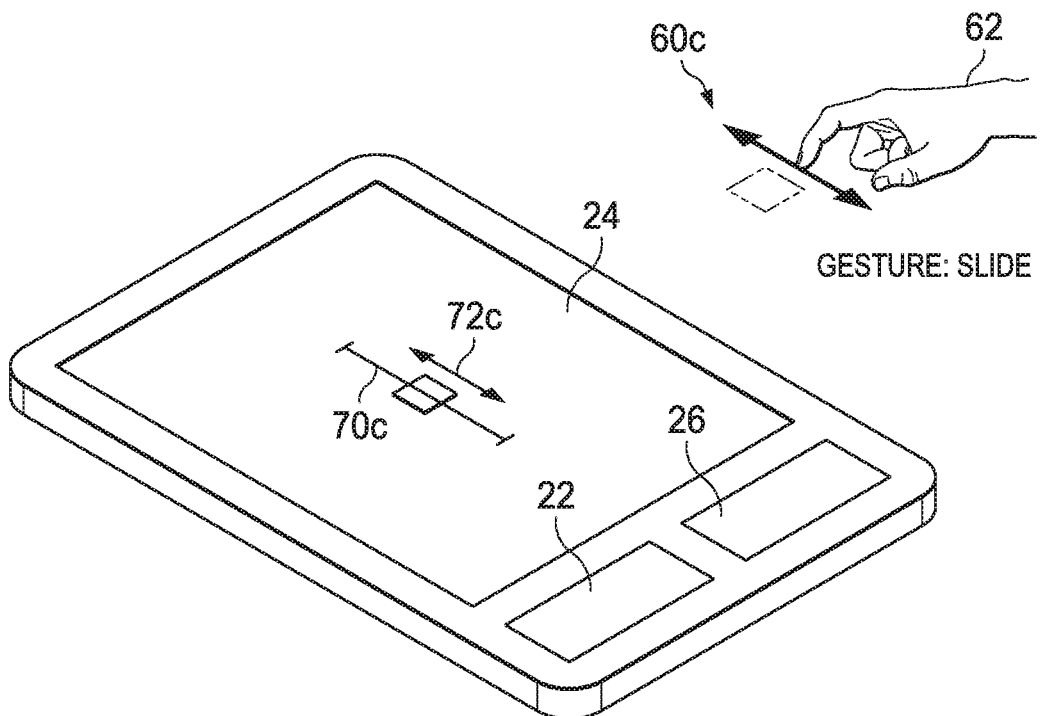

In FIG. 2C, the user controller is a slider that user 62 can slide to select a value indicated by the slider. Haptic sensation generator 22 generates a sensory pattern 60c that operates as the slider. Display 24 displays a slider element 70c representing the slider. User 62 gestures to interact with sensory pattern 60c to slide the slider, e.g., the user moves her hand to slide sensory pattern 60c to select a value indicated by the slider. Display 24 displays a graphic response 72c representing the selection, e.g., the selected value may be highlighted.

Figure 2D:
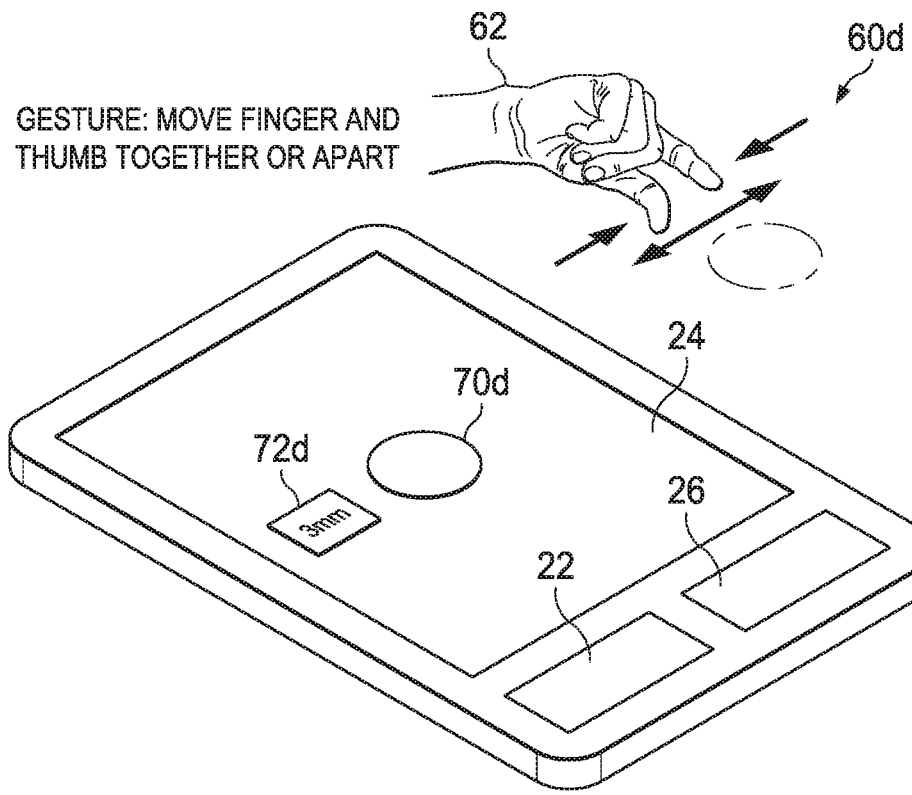

In FIG. 2D, the user controller is a shape comprising one or more objects that user 62 can manipulate to select a distance. For one object, user 62 can squeeze sensory pattern 60 operating as the object to select a smaller distance or expand sensory pattern 60 to select a larger distance. For multiple objects, user 62 can move parts of sensory pattern 60 operating as the objects closer together to select a smaller distance or farther apart to select a larger distance. In the example, haptic sensation generator 22 generates a sensory pattern 60d that represents the shape. Display 24 displays a shape element 70d representing the shape. User 62 gestures to interact with sensory pattern 60d to manipulate the shape. Display 24 displays a graphic response 72d representing the selection, e.g., the selected distance may be displayed.

Figure 2E:
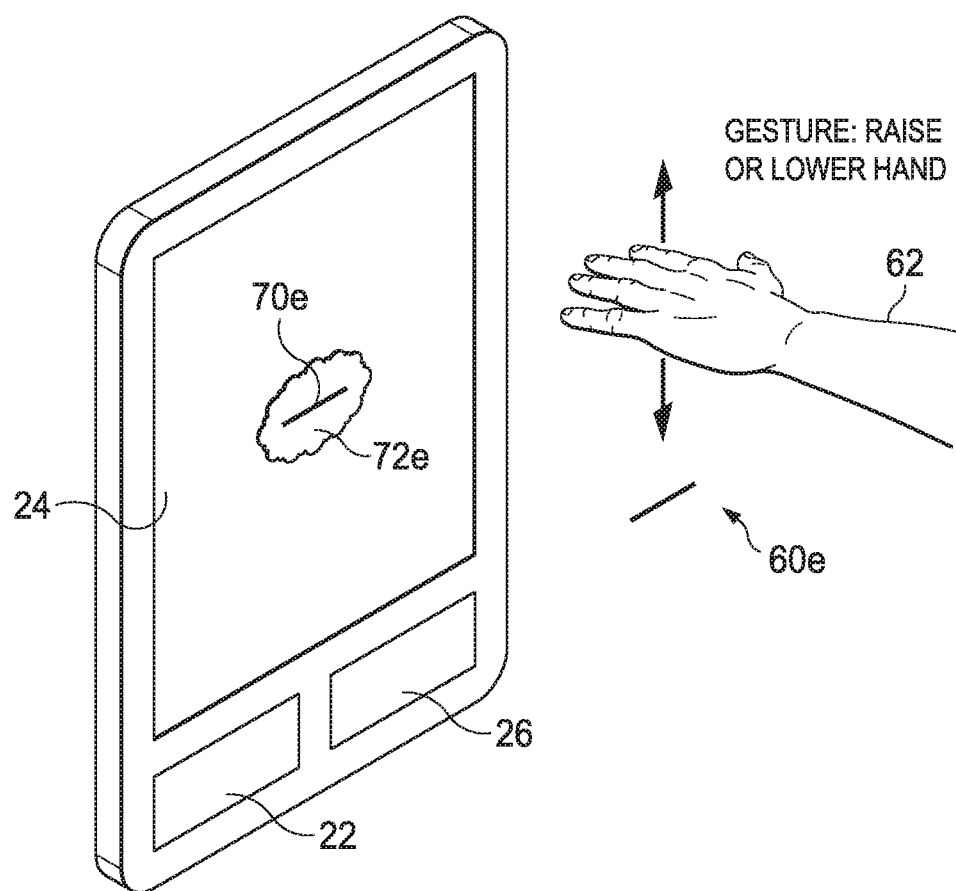

In FIG. 2E, the user controller is a lever that user 62 can raise or lower to select a value indicated by the lever. The value may be the distance between patient support 28 and laser device 20, which may be indicated by the height of patient support 28. Haptic sensation generator 22 generates a sensory pattern 60e that operates as the lever. Display 24 displays a lever element 70e representing the lever. User 62 gestures to interact with sensory pattern 60 to slide the slider, e.g., user 62 moves her hand up or down to raise or lower patient support 28. Display 24 displays a graphic response 72e representing the selection, e.g., the selected value may be highlighted.

Figure 3A:
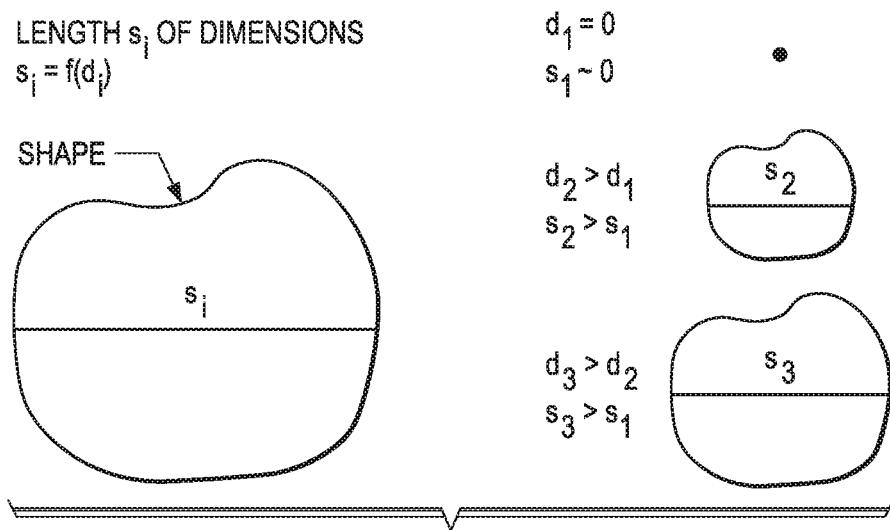
FIGS. 3A-3B illustrate examples of a function that the system of FIG. 1 can apply to determine a sensory pattern.
Figure 3B:
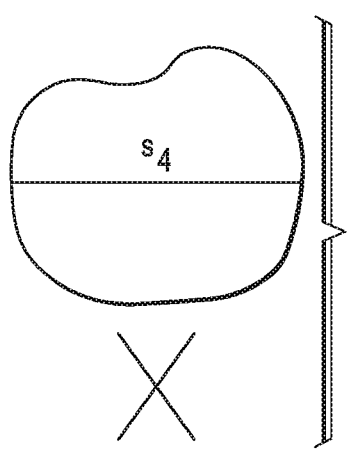

FIGS. 3A-3B illustrate examples of a function that computer 30 can apply to determine a sensory pattern 60. In the examples, a measurement is a variable of the function, so the function can be used to communicate the measurement to user 62 via sensory pattern 60. Any suitable measurement may be used, e.g., a feature of laser beam 40 such a distance to a target. In the examples, the measurement is the distance d between focal point F and target T. The function may be stored in any suitable manner, e.g., as a logical or mathematical operation or in a table. In certain embodiments, display 24 displays a graphic element 70 with the same shape as sensory pattern 60.

In FIG. 3A, given distance d, function f yields a length s of a dimension S of a shape of pattern 60, i.e., s=f(d). Any suitable shape can be used, e.g., a circle, an oval, a square, a rectangle, or a line. Any suitable dimension of the shape can be used, e.g., the diameter of a circle, the longer or shorter diameter of an oval, the side of a square, the longer or shorter side of a rectangle, or the length of a line. A shape may be two or more spots, and the dimension may be the distance between two spots. In the illustrated embodiment, a longer distance d yields a longer length s. That is, given a first distance $d_i$, the function yields a first length $s_i$. Given a second distance $d_j$ greater than the first distance $d_i$, the function yields a second length $s_j$ greater than the first length $s_i$.

In FIG. 3B, function f yields a different shape for certain values of distance d. For example, function f yields a notification alert shape for values of distance d within an alert distance range d*. That is, given a first distance $d_i$ outside of an alert distance range d*, the function yields a pattern with a first shape. Given a second distance $d_k$ within the alert distance range d*, the function yields a pattern with a second shape.

The function f of 3B may be used to alert user 62 if focal point F is too close to target T. For example, the alert distance range d* may be in the range of 0.05 millimeters (mm) to 0.5 mm, such as 0.05 to 0.1, 0.1 to 0.2, 0.2 to 0.3, 0.3 to 0.4, and/or 0.4 to 0.5 mm.

Figure 4:
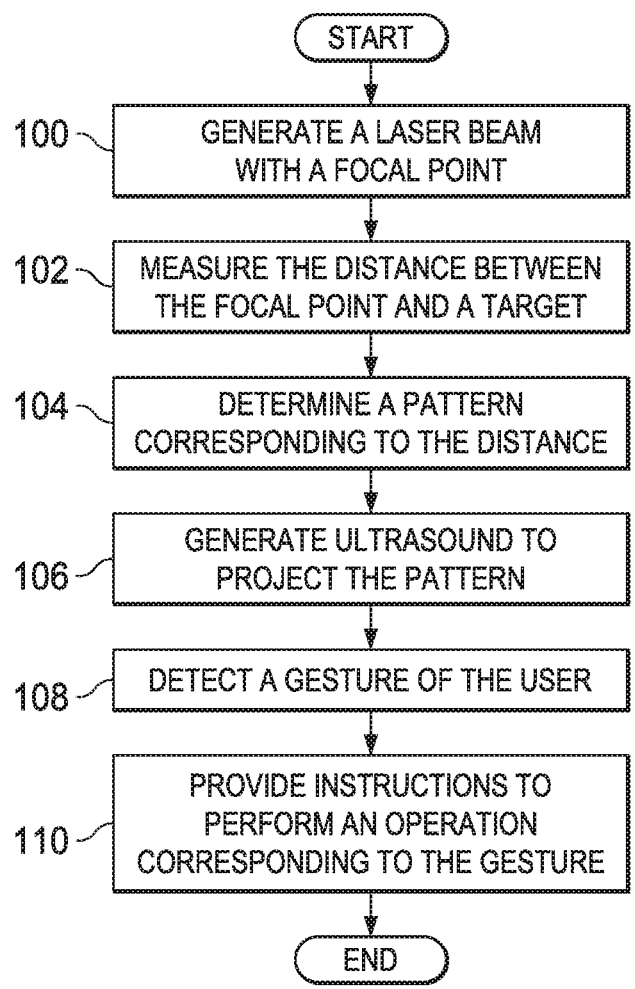
FIG. 4 illustrates an example of a method for providing a measurement and controlling a laser device.

FIG. 4 illustrates an example of a method for providing a measurement and controlling a laser device. The method may be performed by system 10 of FIG. 1. In the method, system 10 notifies user 62 of the distance between laser beam focal point F and target T. User 62 gestures to provide input to system 10, and system 10 performs an operation in response to the input.

The method starts at step 100, where laser device 20 generates laser beam 40 with focal point F. Distance meter 36 measures the distance between focal point F and target T at step 102. Target T may be a point on the surface of eye 50 or a point within tissue, e.g., corneal tissue, of eye 50. In other embodiments, target T may be a point on the surface of the skin or a point within epidermal tissue. At step 104, computer 30 determines sensory pattern 60 corresponding to the distance. Pattern 60 may be determined by using a function, as described with reference to FIGS. 3A-3B. Haptic sensation generator 22 generates ultrasound to project sensory pattern 60 at step 106. Sensory pattern 60 is a tactile sensation that can be felt by, e.g., a human hand of user 62. User 62 makes a gesture that interacts with pattern 60. The gesture may interact with pattern 60 as described with reference to FIGS. 2A-2E. Gesture detector 26 detects the gesture at step 108. At step 110, computer 30 provided instructions to perform an operation corresponding to the gesture. Computer 30 may determine the operation corresponding to the gesture from, e.g., a table. The operation may be performed by a component of system 10.

Figure 5:
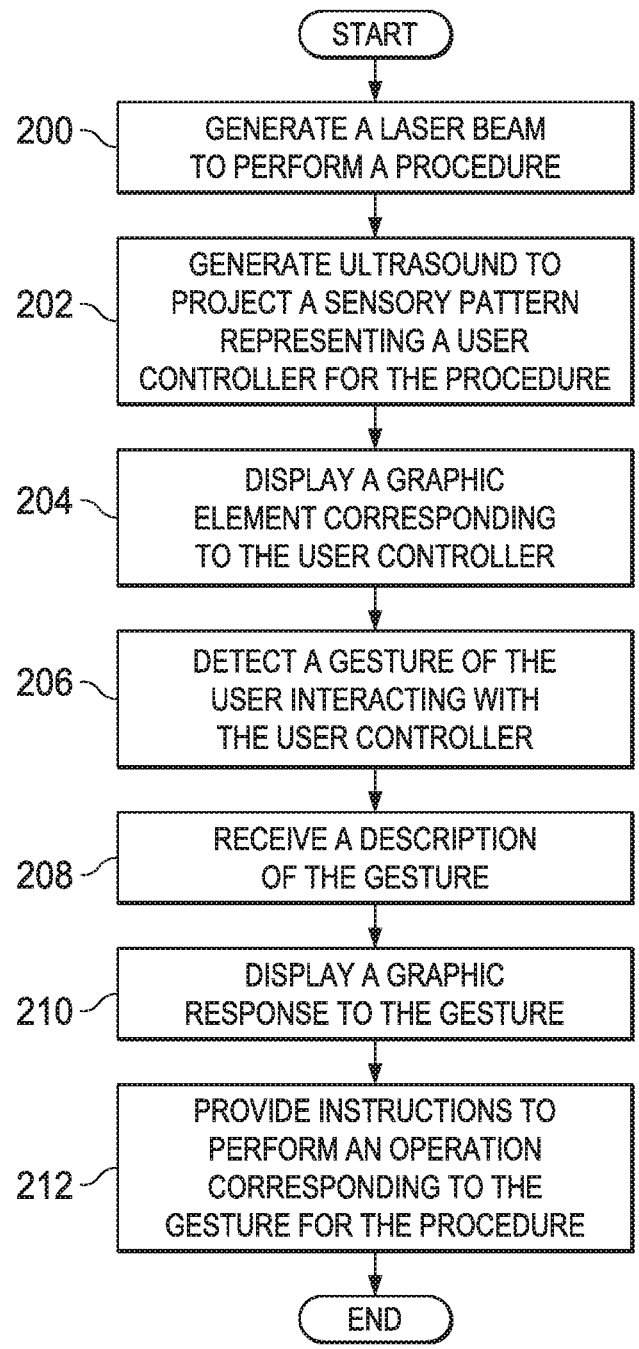
FIG. 5 illustrates an example of a method for controlling a laser device using a haptic sensory pattern.

FIG. 5 illustrates an example of a method for controlling a laser device using a haptic sensory pattern. The method may be performed by system 10 of FIG. 1. In the method, system 10 projects sensory pattern 60 operating as a user controller. User 62 gestures to interact to provide input with the user controller, and system 10 performs an operation to respond to the input.

The method starts at step 200, where laser device 20 generates laser beam 40 to perform a procedure. Haptic sensation generator 22 generates ultrasound to project sensory pattern 60 operating as a user controller for the procedure at step 202. At step 204, display 24 displays graphic element 70 corresponding to the user controller. User 62 can interact with a sensory pattern 60 that corresponds to the user controller in order to send a command to system 10. Gesture detector 26 detects a gesture of user 62 interacting with the user controller at step 206. At step 208, computer 20 receives a description of the gesture from gesture detector 26. Display 24 displays graphic response 72 to the gesture at step 210. At step 212, computer 30 provides instructions to perform an operation corresponding to the gesture for the procedure. Examples of graphic elements 70, sensory patterns 60, gestures, and graphic responses 72 are described with reference to FIGS. 2A-2E.

A component (e.g., computer 30 and device controller computer 38) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors. Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A system for controlling a laser device, comprising:
   the laser device configured to generate a laser beam with a focal point to perform a procedure on a patient at a target location; a distance between the focal point and the target location;
   a haptic sensation generator configured to generate an acoustic field that projects a sensory pattern onto a user, the sensory pattern operating as a user controller related to the procedure, the sensory pattern being a shape with a dimension, a length of the dimension corresponding to the distance between the focal point and the target location, wherein the shape is a circle and the dimension is a diameter of the circle;
   a gesture detector configured to:
      detect a gesture of the user interacting with the user controller; and
      provide a description of the gesture; and
   a computer configured to:
      instruct the haptic sensation generator to generate the acoustic field that projects the sensory pattern operating as the user controller;
      receive the description of the gesture of the user interacting with the user controller; and
      provide instructions to perform an operation corresponding to the gesture.

2. The system of claim 1:
   further comprising a display configured to display a graphic element corresponding to the user controller; and
   the computer configured to instruct the display to:
      display the graphic element; and
      display a graphic response to the gesture of the user interacting with the user controller.

3. The system of claim 1, the computer configured to provide the instructions to the laser device to move the focal point.

4. The system of claim 1, wherein:
   the user controller comprises a command button; and
   the gesture of the user interacting with the user controller comprises selecting the command button.

5. A method for controlling a laser device, comprising:
   generating, with the laser device, a laser beam with a focal point to perform a procedure on a patient at a target location; a distance between the focal point and the target location;
   generating, with a haptic sensation generator, an acoustic field that projects a sensory pattern onto a user, the sensory pattern operating as a user controller related to the procedure, the sensory pattern being a shape with a dimension, a length of the dimension corresponding to the distance between the focal point and the target location, wherein the shape is a circle and the dimension is a diameter of the circle;
   detecting, with a gesture detector, a gesture of the user interacting with the user controller;
   providing, by the gesture detector, a description of the gesture;
   instructing, with a computer, the haptic sensation generator to generate the acoustic field that projects the sensory pattern operating as the user controller;
   receiving, at the computer, the description of the gesture of the user interacting with the user controller; and
   providing, by the computer, instructions to perform an operation corresponding to the gesture;
   wherein the shape is a circle and the dimension is a diameter of the circle;
   wherein the shape is a pair of spots and the dimension is a distance between the pair of spots.

6. The method of claim 5, further comprising:
   displaying, with a display, a graphic element corresponding to the user controller; and
   providing, by the computer, instructions to the display to:
      display the graphic element; and
      display a graphic response to the gesture of the user interacting with the user controller.

7. The method of claim 5, further comprising providing, by the computer, instructions to the laser device to move the focal point.

8. The method of claim 5, wherein:
the user controller comprises a command button; and
the gesture of the user interacting with the user controller comprises selecting the command button.

9. A system for controlling a laser device, comprising:
the laser device configured to generate a laser beam with a focal point to perform a procedure on a patient at a target location; a distance between the focal point and the target location;
a haptic sensation generator configured to generate an acoustic field that projects a sensory pattern onto a user, the sensory pattern operating as a user controller related to the procedure, the sensory pattern being a shape with a dimension, a length of the dimension corresponding to the distance between the focal point and the target location, wherein the shape is a pair of spots and the dimension is a distance between the pair of spots;
a gesture detector configured to:
   detect a gesture of the user interacting with the user controller; and
   provide a description of the gesture; and
a computer configured to:
   instruct the haptic sensation generator to generate the acoustic field that projects the sensory pattern operating as the user controller;
   receive the description of the gesture of the user interacting with the user controller; and
   provide instructions to perform an operation corresponding to the gesture.

10. The system of claim 9:
further comprising a display configured to display a graphic element corresponding to the user controller; and
the computer configured to instruct the display to:
   display the graphic element; and
   display a graphic response to the gesture of the user interacting with the user controller.

11. The system of claim 9, the computer configured to provide the instructions to the laser device to move the focal point.

12. The system of claim 9, wherein:
the user controller comprises a command button; and
the gesture of the user interacting with the user controller comprises selecting the command button.

13. A method for controlling a laser device, comprising:
generating, with the laser device, a laser beam with a focal point to perform a procedure on a patient at a target location; a distance between the focal point and the target location;
generating, with a haptic sensation generator, an acoustic field that projects a sensory pattern onto a user, the sensory pattern operating as a user controller related to the procedure, the sensory pattern being a shape with a dimension, a length of the dimension corresponding to the distance between the focal point and the target location, wherein the shape is a pair of spots and the dimension is a distance between the pair of spots;
detecting, with a gesture detector, a gesture of the user interacting with the user controller;
providing, by the gesture detector, a description of the gesture;
instructing, with a computer, the haptic sensation generator to generate the acoustic field that projects the sensory pattern operating as the user controller;
receiving, at the computer, the description of the gesture of the user interacting with the user controller; and
providing, by the computer, instructions to perform an operation corresponding to the gesture;
wherein the shape is a circle and the dimension is a diameter of the circle;
wherein the shape is a pair of spots and the dimension is a distance between the pair of spots.

14. The method of claim 13, further comprising:
displaying, with a display, a graphic element corresponding to the user controller; and
providing, by the computer, instructions to the display to:
   display the graphic element; and
   display a graphic response to the gesture of the user interacting with the user controller.

15. The method of claim 13, further comprising providing, by the computer, instructions to the laser device to move the focal point.

16. The method of claim 13, wherein:
the user controller comprises a command button; and
the gesture of the user interacting with the user controller comprises selecting the command button.

* * * * *